United States Patent [19]
Lunn

[11] Patent Number: 5,476,506
[45] Date of Patent: Dec. 19, 1995

[54] BI-DIRECTIONAL CRIMPED GRAFT

[75] Inventor: Anthony C. Lunn, Princeton, N.J.

[73] Assignee: Ethicon, Inc., Somerville, N.J.

[21] Appl. No.: 193,314

[22] Filed: Feb. 8, 1994

[51] Int. Cl.$^6$ ..................................................... A61F 2/06
[52] U.S. Cl. ..................... 623/1; 623/9; 623/12
[58] Field of Search ..................... 623/1, 12, 9; 606/192, 606/194, 195, 197

[56] References Cited

U.S. PATENT DOCUMENTS

| | | | |
|---|---|---|---|
| 3,688,317 | 9/1972 | Kurtz | 623/1 |
| 3,878,565 | 4/1975 | Sauvage | 623/1 |
| 4,164,045 | 8/1979 | Bokros et al. | 128/334 |
| 4,313,231 | 2/1982 | Koyamada | 623/1 |
| 4,545,082 | 10/1985 | Hood | 623/1 |
| 4,787,899 | 11/1988 | Lazarus | 623/1 |
| 4,816,028 | 3/1989 | Kapadia et al. | 623/1 |
| 5,108,424 | 4/1992 | Hoffman et al. | 623/1 |
| 5,282,847 | 2/1994 | Trescony et al. | 623/1 |
| 5,306,294 | 4/1994 | Winston et al. | 623/1 |
| 5,366,473 | 11/1994 | Winston et al. | 623/12 |

*Primary Examiner*—David H. Willse
*Assistant Examiner*—Bruce E. Snow
*Attorney, Agent, or Firm*—Paul A. Coletti

[57] ABSTRACT

This invention relates to a graft for placement in a body passageway. The graft comprises a longitudinally extending thin walled cylinder having first and second open ends. The graft is divided into first and second axially extending end portions adjacent such open ends and an axially extending central portion therebetween. The walls of the central portion are provided with circumferential crimps and the wall of the end portions are provided with axially extending crimps whereby the central portion can be extended longitudinally to vary the distance between the end portions and the end portions may be expanded radially to vary the diameter of the end portions. In preferred embodiment the end portions have a greater diameter than the central portion imparting to the graft a somewhat dumbbell like shape preferable in employing the graft in the reduced diameter lumen of a diseased blood vessel.

21 Claims, 4 Drawing Sheets

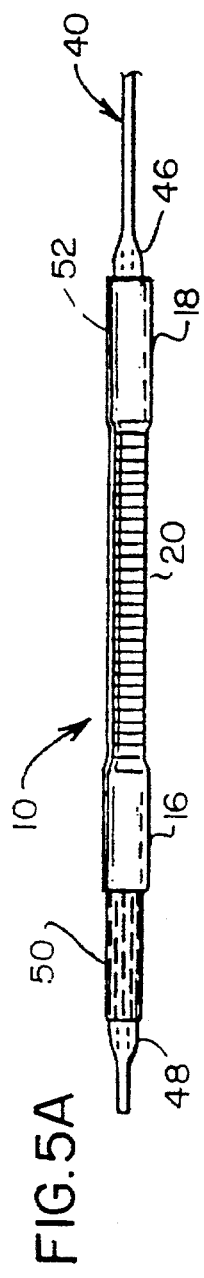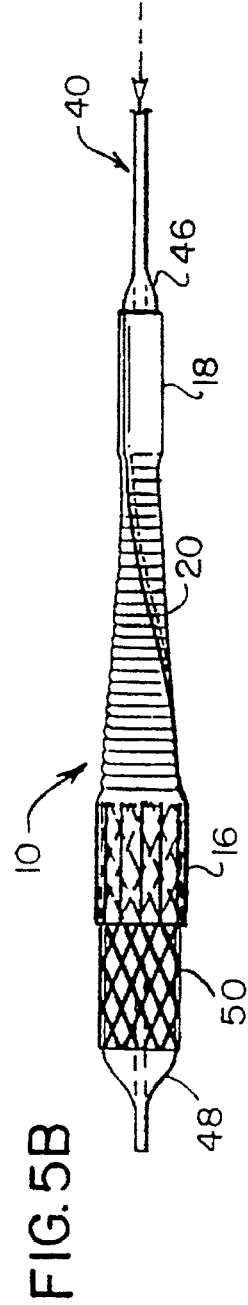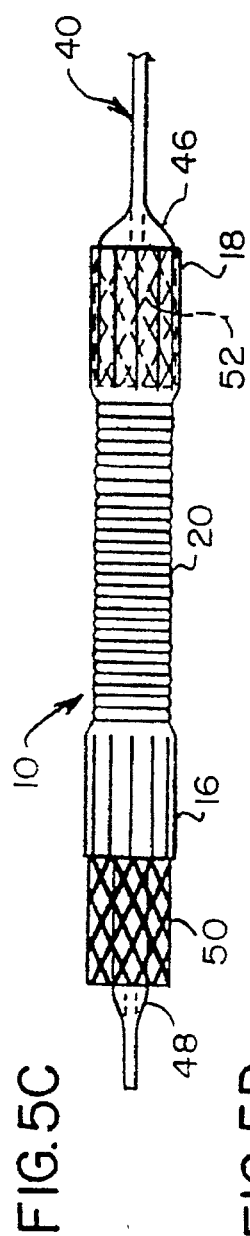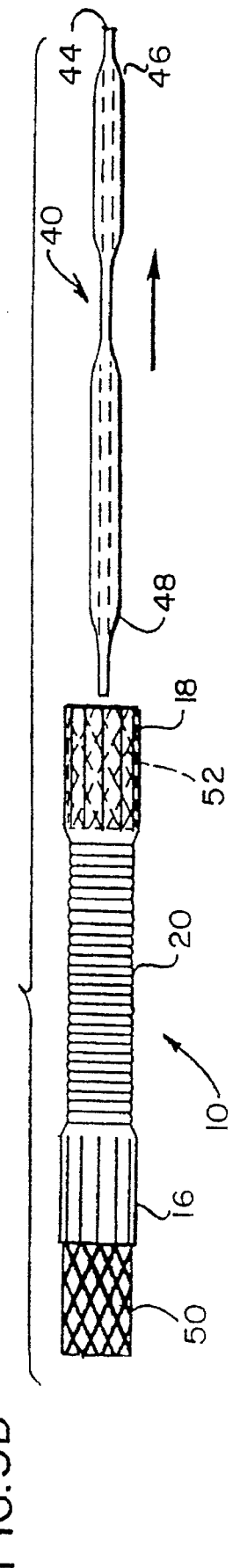

BI-DIRECTIONAL CRIMPED GRAFT

BACKGROUND OF THE INVENTION

This invention relates generally to prostheses for repairing diseased or damaged sections of a body passageway and more specifically to vascular grafts for repair of damaged or diseased sections of body vessels such as blood vessels.

Diseased or damaged blood vessels which may weaken, develop into aneurysms and rupture have conventionally been treated by invasive surgical techniques which surgically expose the section to be repaired. The section is resected and replaced either by a section of healthy vessel removed from some other site of the patient or by a tubular synthetic graft. The graft is sutured in place. Alternatively, it has been suggested in U.S. Pat. Nos. 3,657,744 and 5,078,726, that the graft be held in place by stents disposed inside the end portions of the graft and expanded to firmly affix the end portion walls of the graft between the expanded stent and the vessel walls.

Recently, it has been suggested to replace the invasive surgical techniques and the treatment of diseased or damaged iliac or aortic vessels with so-called minimally invasive or interventional procedures whereby a small incision in a femoral artery of the patient is made and the graft-stent combination is delivered to the desired site by way of catheterization. Once delivered, the graft is affixed in place by expanding the stent and, in order to do this without invasive surgery, such expansion is accomplished by use of one or more angioplasty-like balloon catheters with the inflation balloon or balloons employed to expand each of these stents. Such systems and suggestions are described in U.S. Pat. Nos. 4,577,631 and 5,078,726.

As described in the above-cited patents, the tubular graft is inserted into the vessel and is of a length sufficient to span the weakened sections of the blood vessel to be repaired and to overlap the healthy sections on either side of the weakened section. Once emplaced, the ends of the graft are affixed to the healthy sections by expanding a stent placed therein. The length of the weakened section will of course, vary from case to case. Because it is desirable to employ a length of graft which is sufficient to span the weakened section and only a minimal length of healthy sections necessary for good retention, reasonably close tolerances are necessary in properly choosing a length of graft to be employed. Ultimately, irrespective of the length provided by the manufacturer or selected by the doctor, fine adjustments must be made in a length in order to properly emplace the graft. Heretofore, these adjustments have been accomplished by virtue of the longitudinal elasticity, if any, present in the materials of construction from which the grafts are manufactured. Since such elasticity is relatively limited and, in some cases, nonexistent, the great burden of choosing the proper length of graft has been left to the skill of the doctor and frequently has presented the doctor with difficulties.

A similar problem exists at the ends of the graft wherein the ends of the graft are held in place by being sandwiched between the healthy portion of the blood vessel and an expanded stent. In order to do this, the end portions of the graft must be such that they can be affixed to the stent when the stent is unexpanded and then increased in diameter, together with the stent as the stent is expanded towards the walls of the blood vessel. Accordingly, the ends of the graft must also have elasticity, albeit radial elasticity. Again, while to a degree and some graft materials are inherently elastic in the radial direction, it is important to increase the degrees of freedom in choosing a proper graft size. Therefore, it is desirable for the manufacturer to provide the doctor with a wider range of elastic expansion than is assured by reliance on the inherent elasticity of the graft materials of construction.

Accordingly, there is a need for a graft which provides great freedom of both longitudinal and radial expansion at the central and end portions, respectively.

SUMMARY OF THE INVENTION

In accordance with the teachings herein, a graft is provided which has longitudinal elasticity whereby the doctor employing the same may adjust the length of the graft within wide limits that are virtually independent of the materials of construction. Further, the graft is provided at its end portions with radial elasticity whereby the end portions may be expanded to diameters by such graft affixing devices as stents wherein such expansion again is virtually independent of the materials of construction.

Consistent with the teachings herein, such a graft is provided for placement in a body passageway, the graft comprising a longitudinally extending thin walled hollow cylinder having first and second open ends. The graft is divided into first and second axially extending end portions adjacent such first and second open ends, respectively, and an axially extending central portion therebetween. The walls of the central portion are provided with circumferential crimps and the walls of the end portion are provided with axially extending crimps whereby the central portion can be extended longitudinally from its relaxed position to vary the distance between the end portions. The circumferential crimps serve also to render the central portion of the graft more flexible and capable of conforming to curves in the vascular system without undesirable kinking. The end portions may be expanded radially to vary the diameter of said end portions as is advantageous, when affixing such end portions with an expandable stent. In a preferred embodiment the end portions have greater diameter in the relaxed state than the central portion, imparting to the graft a somewhat dumbbell shape. Such shape is preferable in that it most closely resembles the shape of the lumen of a diseased section of blood vessel and hence, avoids kinks and folds which would otherwise occur in a graft of uniform diameter as it conforms to the lumen of the blood vessel.

BRIEF DESCRIPTION OF THE DRAWINGS

FIGS. 5a through 5d are schematic elevational views of the graft of FIG. 1 mounted on a balloon catheter delivery system in various stages in the course of emplacing such graft into a blood vessel.

DETAILED DESCRIPTION OF THE INVENTION

Figure 1:
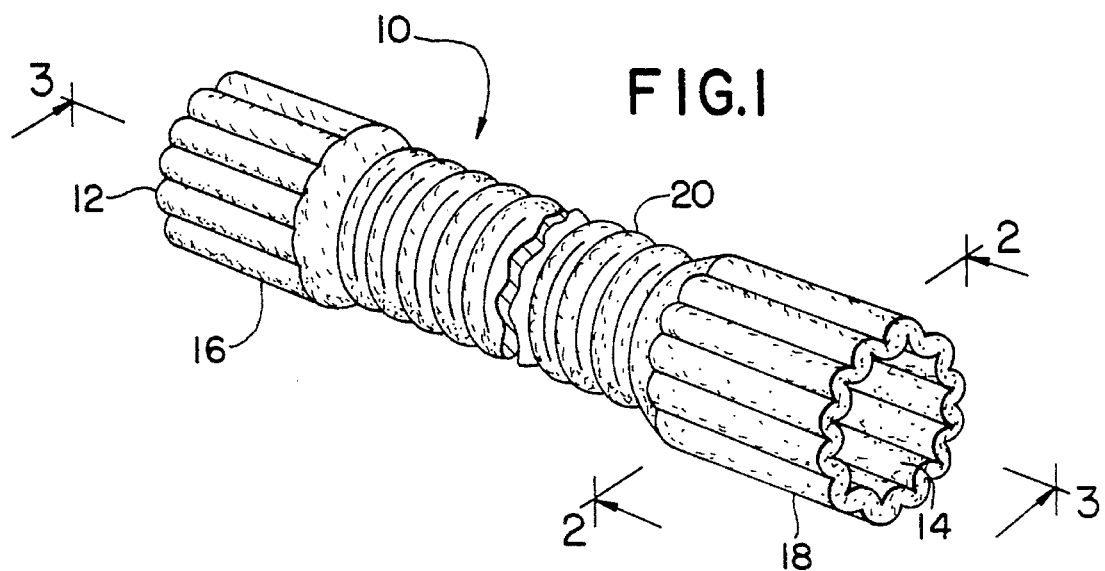
FIG. 1 is a perspective view of a graft embodying the teaching of this invention.
Figure 2:
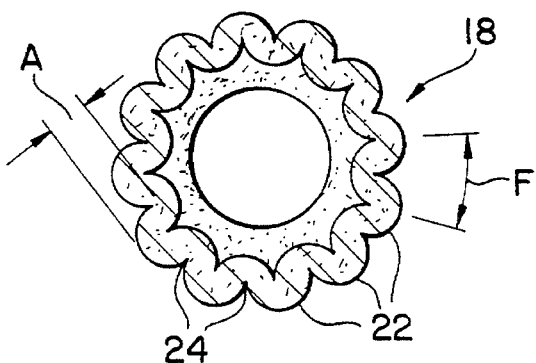
FIG. 2 is a transverse cross sectional view of an end portion of the graft of FIG. 1, taken through line 2—2 of FIG. 1.
Figure 3:
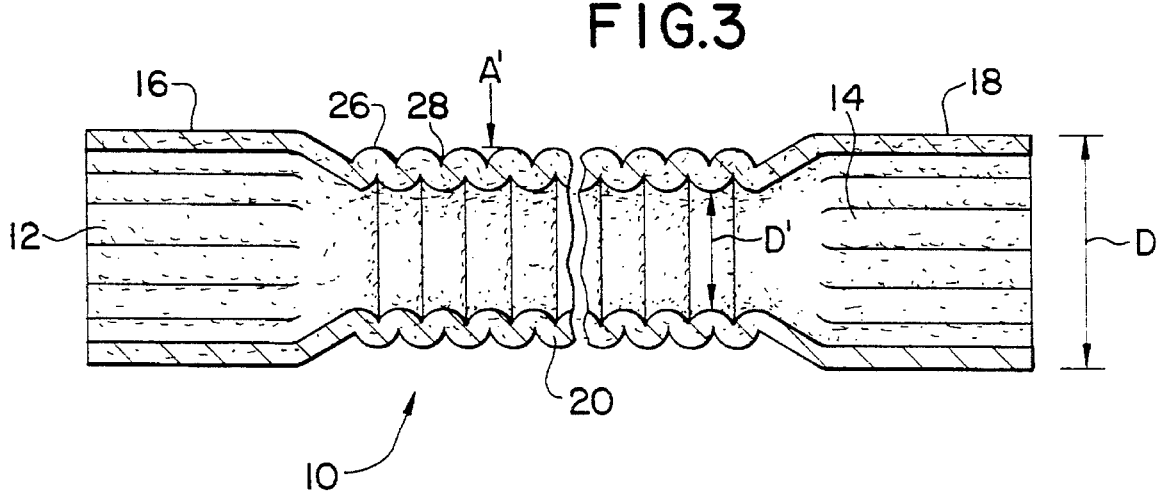
FIG. 3 is an axially extending, cross sectional view of the graft of FIG. 1, taken through line 3—3 of FIG. 1.

Referring now to the drawings, FIGS. 1–3 illustrate an embodiment of the graft of this invention as shown in the relaxed state. The graft 10 is generally a thin walled hollow cylinder having a first open end 12 and a second open end 14. The graft is divided into ends portion 16 and 18 adjacent open ends 12 and 14 respectively, with central portion 20 therebetween.

As best viewed in FIG. 2, the end portion 18 is provided with a series of longitudinally extending pleats or crimps each comprised of a ridge 22 and a trough 24. End portion 16, likewise is comprised of such crimps. The crimps thereby provide the end portion with a great degree of freedom in expanding the end portion to a selected diameter. The preferred geometry of the crimp may best be described in terms of the height of the crimp or "amplitude" and the distance between heights or "frequency" parameters.

The amplitude, shown in FIG. 2 as the dimension A, is expressed as a percentage of the trough diameter of the end portion in the relaxed state i.e., the diameter taken from trough to diametrically opposed trough. It is believed that a preferred value for the amplitude ranges from about three percent to almost twenty percent of the trough diameter and preferably from about five percent to about fifteen percent of the trough diameter. Thus, for example, when trough diameters, as may be typically employed, range from 26 to 30 mm at the end portion of the graft, the height of the crimps or amplitudes may vary from about 0.78 mm to 6 mm and preferably, from about 1.3 mm to about 4.5 mm e.g., for example, a trough amplitude of 2 mm.

The frequency, shown in FIG. 2 as the dimension F, is expressed as the distance between ridges 22 when the end portions are in the relaxed state. It is believed that preferred values for the frequency range from about 0.3 mm to about 5 mm and preferably from about 1 mm to about 3 mm.

When adhering to the broadest range of the above described parameters, the circumference of the graft at the end portions may be increased from a range of 10 to 300 % of the trough circumference (i.e., the circumference of the circle comprising the bottom of the troughs on the outer surface of the graft). Accordingly, the doctor when employing a balloon expanded stent to affix the graft will have a wide and, for practical purposes, an infinite degree of freedom in expanding to a diameter which will best suit the particular site of affixation.

As best viewed in FIG. 3, the central portion 20 is provided with a series of circumferential crimps each of which are comprised of a ridge 26 and a trough 28. These crimps thereby provide the central portion with a great degree of freedom in extending the central portion to a selected length to conform to the site of application. Again the geometry of these circumferential crimps is best described in terms of the height of the crimp or "amplitude" and the distance between heights or "frequency" parameters.

The amplitude for the central portion, shown in FIG. 3 as the dimension A', is again expressed as a percentage of the trough diameter of the central portion in the relaxed state and may vary through essentially the same range of values as for the end portions i.e., from about three to twenty percent and preferably from about five to fifteen percent. Similarly, the frequency, shown in FIG. 3 as the dimension F', is expressed as the distance between ridges 26 when the central portion is in the relaxed state. Again it is believed that preferred values for the frequency in the central portion may range from about 0.3 mm to about 5 mm and preferably from about 1 mm to about 3 mm.

When adhering to the above parameters, the central portion may be expanded in length, from about 10 to about 200 percent, based on the length of the crimped central portion in its unexpanded state. Accordingly the doctor, employing a single sized graft, may accommodate a wide variety of grafting applications.

It should be understood that while the exemplified embodiment has been illustrated with specific geometry, a wide variation is possible within the broad teachings of this invention. For example, while the crimps in the central portions and in the end portions have been illustrated as having uniform amplitude and frequency, in certain instances it may be preferable to vary these parameters within a given portion or even to omit crimping in certain sections of a given portion.

As best illustrated in FIGS. 1 and 3, the end portions 16 and 18 of the graft 10 have greater diameters in the relaxed state than the central portion 20, thereby imparting the graft with a somewhat dumbbell-like shape. Such a shape is preferable in that it most closely resembles the shape of the lumen in the grafted section of a diseased blood vessel (i.e., the section comprising the healthy portions of the vessel and the diseased portion there between) and hence avoids kinks and folds which would otherwise occur in a graft of uniform diameter as it conforms to the lumen of the blood vessel.

Figure 4:
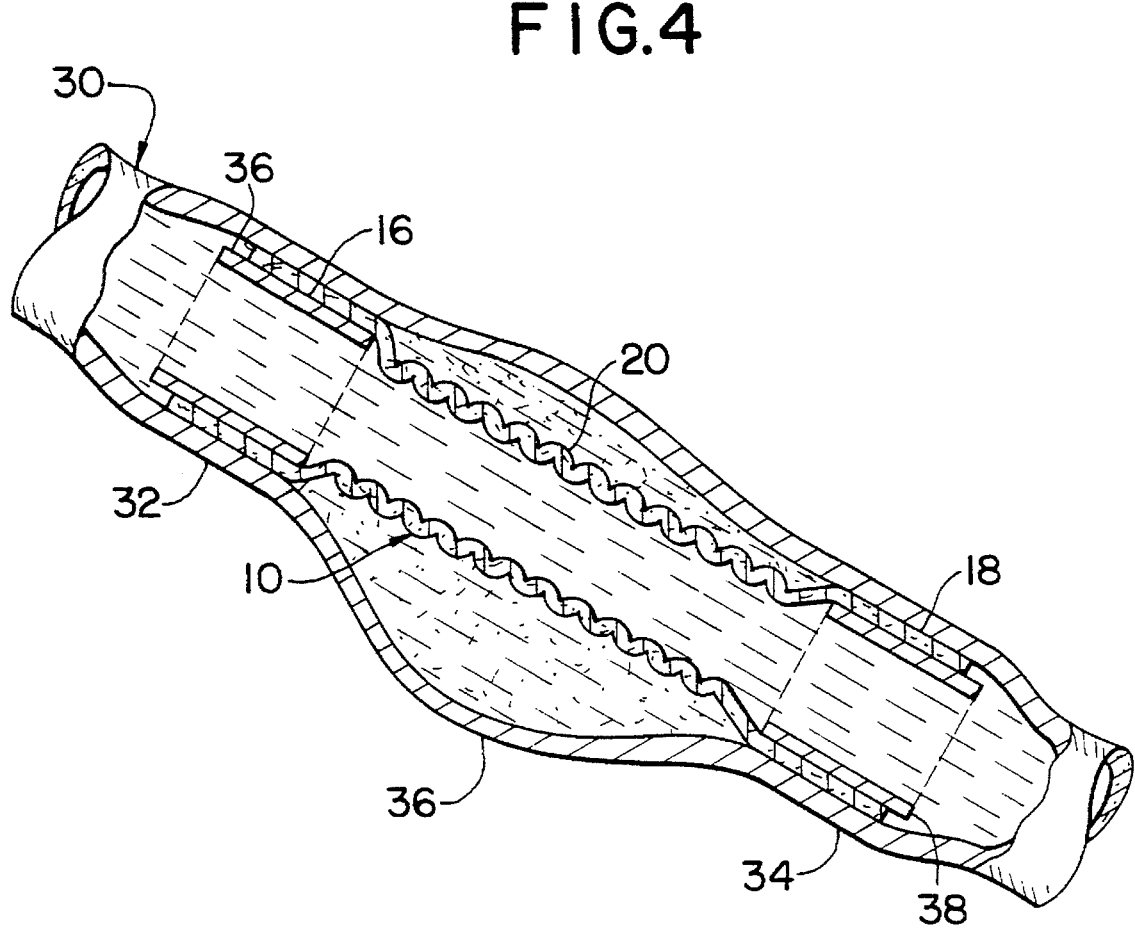
FIG. 4 is a schematic axially extending cross sectional view of the graft of FIG. 1 placed within a diseased blood vessel.

Referring to FIG. 4, illustrated therein is an emplaced graft 10 of this invention in a blood vessel 30. As illustrated, the end portion 16 and 18 are employed, respectively, in healthy sections 32 and 34 of the vessel 30 and the stents 36 and 38 expanded to sandwich the walls of the end portions 16 and 18 between the stents and the vessel walls so as to affix the graft in place. As is typical, the diseased portion 36 of vessel 30 displays an aneurysm i.e., a weakened, expanded wall. Additionally, as shown, the space between the graft and the aneurysm wall is filled with a gel-like clot, known as mural thrombus, which greatly decreases the lumen size in the diseased portion of the vessel as contrasted to the lumen size in the healthy portion. Accordingly, if the central portion of the graft is sized to have the same diameter as the end portions, when the central portion is emplaced, in order to conform to the reduced lumen size, the central portion must undesirably kink or fold. However, in accordance with the teachings herein, because of the dumbbell-like shape of the preferred graft of this invention, such kinking and folding is avoided.

Referring back to FIG. 3, the geometrical parameters relating to the preformed dumbbell shape are best described in terms of the ratio of the largest ridge diameter of the largest end portion (D in FIG. 3) to the smallest ridge diameter of the central portion (D' in FIG. 3), wherein ridge diameter is the distance between the outer surface of a ridge to the outer surface of its diametrically opposed ridge (it should be noted that the end portions need not have the same ridge diameter and that the diameter within either end portion or the central portion does not necessarily have to be uniform). It is believed that this ratio may vary from about 1.1 to about 4 and preferably from about 1.2 to about 1.4. Thus, for example, for a central portion ridge diameter of 22 mm, the end ridge diameter preferably may vary from about 24 to about 30 mm.

Referring to FIGS. 5a–5d and FIGS. 6a and 6b, illustrated therein schematically is the graft of this invention mounted on a double balloon catheter 40 and the method of employing the graft. As best seen in the right hand portion of FIG. 5d, the catheter 40 comprises a hollow tube 42 having a lumen therethrough 44. Affixed to the catheter tube 42 are two expansion balloons 46 and 48. The balloons are capable of being expanded by the action of introducing, under pressure, an expanding fluid such as air or water from a remote source and being deflated by depressuring such fluid. The means for so introducing fluid remotely through the catheter to the balloons are well known in the art of angioplasty balloon catheters and stent delivery systems and hence are not illustrated in the drawings for the sake of simplicity.

Figure 6A:
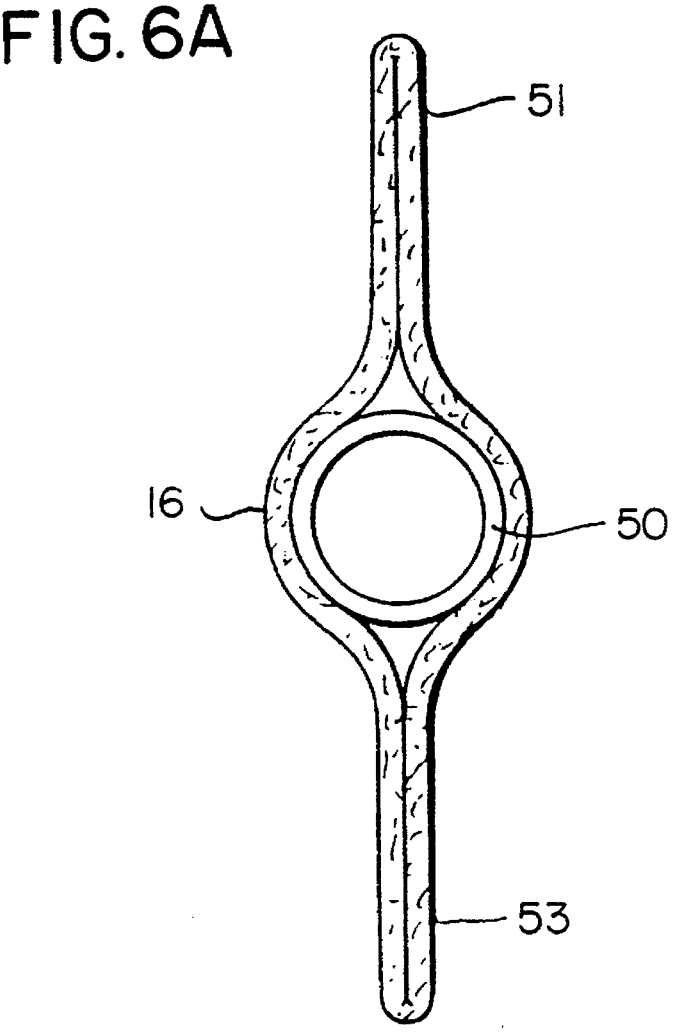
FIGS. 6a and 6b are transverse cross sectional views illustrating one method of carrying the graft on the delivery system.
Figure 6B:
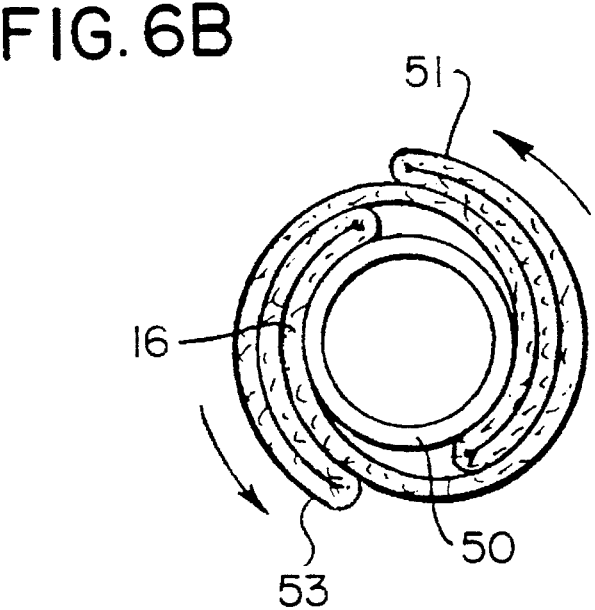

As illustrated in FIGS. 6a and 6b, each end portion of the graft 10 (crimping omitted for clarity) is affixed to an expandable stent 50 by such means as suturing or employing an adhesive, staples, barbs, pins, or the like. Because the graft diameter is substantially larger than the unexpanded stent 50, it is desirable to fold the end portions of the graft 51, 53 about the stent 50 (and consequently fold the central portion 20 about the catheter). Such folding is illustrated in FIG. 6b wherein the projecting ends of the graft 51, 53 are first folded flat (FIG. 6a) and then wrapped about the stent 50 (and about the catheter in the central portion) in an s-shaped configuration (FIG. 6b). This folding greatly facilitates the unfolding of the graft upon expansion so as to be free of kinks and folds when emplaced.

Referring to FIG. 5A, the graft, with its end portions 16 and 18 affixed to stents 50 and 52, is folded as illustrated in FIG. 6b and is mounted on the catheter 40. Stent 50 is mounted on the unexpanded balloon 48 and stent 52 is mounted on the unexpanded balloon 46 with the central portion 20 of the graft folded about the catheter. The catheter, with the mounted stent-graft assembly, is then introduced into the body of the patient as, for example, through the femoral artery. The catheter is manipulated through the vascular system of the patient until the lead balloon 48 is in the correct position e.g., the cranial healthy portion of a diseased aorta. The doctor then expands the balloon 48, which in turn expands the stent 50 and the leading end portion 16 of the graft as illustrated in FIG. 5b. Because of the longitudinal crimps provided in such end portion 16 the doctor has the freedom to expand this end portion to precisely the degree required to trap and affix the walls of the graft between the walls of the cranial healthy portion of the vessel (not shown) and the stent.

Next, with the expanded stent 50 and the end portion 16 firmly affixed, the doctor deflates the balloon 48 and extends the central portion 20 of the graft proximally to locate the balloon 46 and its associated stent 52 and end portion 18 in the desired position on the caudal healthy portion of the vessel. Because of the circumferential crimps provided in the central portion, the doctor has the freedom to locate end portion 18 in precisely the desired position. The balloon 46 is then expanded to expand stent 52 and trap and affix end portion 18 between the expanded stent 52 and the wall of the caudal healthy portion of the vessel (also not shown). This step is illustrated in FIG. 5c.

Finally, the doctor deflates balloon 46 and removes the catheter from the patient, leaving graft 10 in place as is illustrated in FIG. 5d.

The graft of this invention may be constructed of a variety of materials such as are now employed for vascular grafts. Such materials may be in the form of films and yarns, woven or knitted into hollow cylinders, and employing such naturally occurring polymers such as cellulose or silk. Additionally synthetic polymers such as polyolefins e.g. polyethylene, polypropylene; polyethylene terephthalate; nylon; polytetrafluoroethylene or polyurethene may be employed. In addition to weaving or knitting yarns into cylinders, the cylinders may be formed by other methods known in the art such as by molding or extrusion. The crimping may be introduced by molding about an appropriately shaped mold or by first forming an uncrimped cylinder and then shrinking the cylinder about an appropriately shaped mandrel. Woven, knitted or otherwise shaped cylinders may be shrunk in such manner about a mandrel by means of heat shrinking, chemical shrinking means or by a combination of heat and water. The material of choice is polyethylene terephthalate which is woven into a cylinder having the requisite dumbbell shape. The central portion is then shrunk about a mandrel to introduce the circumferential crimp. Appropriate mandrels are then inserted into the end portion which are then shrunk to introduce the longitudinal crimps and the finished graft is then removed from the mandrels which may come apart for ease in removal.

What is claimed is:

1. A tubular graft for a body passageway comprising a longitudinally extending thin walled hollow cylinder having first and second open ends, first and second end portions adjacent said first and second open ends, respectively, and a central portion longitudinally extending between said end portions;

the walls having circumferential crimps solely in said central portion and longitudinally extending crimps solely in said end portions;

whereby said central portion can be extended longitudinally from its relaxed position to vary the distance between the end portions and the end portions can be extended radially to vary the diameter of said end portions.

2. The graft of claim 1 wherein said crimps in said portions each comprise a ridge and a trough defining an amplitude, a frequency, a trough diameter and a ridge diameter.

3. The graft of claim 2 wherein the amplitude of the crimp in at least one said end portion, in the relaxed state ranges from about three percent to about twenty percent of the trough diameter of said crimps.

4. The graft of claim 3 wherein the amplitude of the crimp in said end portion in the relaxed state ranges from about five to about fifteen percent of the trough diameter of said crimps.

5. The graft of claim 2 wherein the frequency of the crimps in at least one of said end portions, in the relaxed state, ranges from about 0.3 mm to about 5 mm.

6. The graft of claim 5 wherein the frequency of the crimps in at least one of said end portions, in the relaxed state, ranges from about 1 mm to about 3 mm.

7. The graft of claim 2 wherein the amplitude of the crimps in at least one said end portion, in the relaxed state, ranges from about three percent to about twenty percent of the trough diameter of said crimp and the frequency of the crimps of said end portion, in the relaxed state, ranges from about 0.3 mm to about 5 mm.

8. The graft of claim 2 wherein the amplitude of the crimps in the central portion, in the relaxed state, ranges from about three to about twenty percent of the trough diameter of said crimps.

9. The graft of claim 8 wherein the amplitude of the crimps in the central portion, in the relaxed state, ranges from about five to about fifteen percent of the trough diameter of said crimps.

10. The graft of claim 2 wherein the frequency of the crimps in the central portion, in the relaxed state, ranges from about 0.3 mm to about 5 mm.

11. The graft of claim 10 wherein the frequency of the crimps in the central portion, in the relaxed state, ranges from about 1 mm to about 3 mm.

12. The graft of claim 2 wherein the amplitude of the crimps in the central portion, in the relaxed state, ranges from about three to about twenty percent of the trough diameter of said crimp and the frequency of the crimps in the central portion, in the relaxed state, ranges from about 0.3 mm to about 5 mm.

13. The graft of claim 2 wherein the crimps in at least one said end portion and the crimps in said central portion, in the relaxed state, have an amplitude ranging from about three percent to about twenty percent of the trough diameter of said crimps and a frequency, in the relaxed state, ranging from about 0.3 to about 5 mm.

14. The graft of claim 2 wherein, in the relaxed state, the end portions of the graft each comprises crimps having greater ridge diameter than the smallest ridge diameter of crimps in the central portion.

15. The graft of claim 14 wherein the ratio of said greater ridge diameter to said smallest ridge diameter ranges from about 1.4 to about 4.

16. The graft of claim 15 wherein the ratio of said greater ridge diameter to said smallest ridge diameter range from about 1.2 to about 1.4.

17. The graft of claim 1 wherein at least one said end portion is mounted over an expandable stent.

18. The graft of claim 17 wherein both end portions are each mounted over separate expandable stents.

19. The graft of claim 17 wherein said graft and expandable stent are mounted over a balloon catheter with said expandable stent mounted over the balloon.

20. The graft of claim 18 wherein said graft and expandable stents are mounted over a double balloon catheter with each of said expandable stent mounted over a balloon of said catheter.

21. A tubular graft for a body passageway comprising longitudinally extending thin walled hollow cylinder having first and second open ends, first and second end portions adjacent said first and second open ends, respectively, and a central portion longitudinally extending between said end portions;

the walls of said central portion having circumferential crimps and said end portions having longitudinally extending crimps, said crimps in said central and end portions each comprising a ridge and a trough defining an amplitude, a frequency, a trough diameter and a ridge diameter;

the amplitude of the crimps in at least one of said end portions, in the relaxed state, ranging from about three percent to about twenty percent of the trough diameter of said crimp in said end portions and the frequency of the crimp in said end portion, in the relaxed state, ranging from about 0.3 to about 5 mm;

the amplitude of the crimp in the central portion, in the relaxed state, ranging from about three percent to about twenty percent of the trough diameter of said crimp in said central portion and the frequency of the crimp in said central portion in the relaxed state ranging from about 0.3 to about 5 mm;

wherein, in the relaxed state, the end portions of the graft each comprise crimps having a greater ridge diameter than the smallest ridge diameter of crimps in the central portion and wherein the ratio of said greater ridge diameter to said smallest ridge diameter ranges from about 1.4 to about 4.

* * * * *